(12) United States Patent
Watson et al.

(10) Patent No.: US 9,877,651 B2
(45) Date of Patent: Jan. 30, 2018

(54) INTERMITTENT OPERATING BATTERY-LESS WIRELESS SENSOR AND PULSE OXIMETER

(71) Applicant: Covidien LP, Mansfield, MA (US)

(72) Inventors: James N. Watson, Denfermline (GB); Paul S. Addison, Edinburgh (GB); James H. Dripps, West Linton (GB); George Keith Manning, Linlithgow (GB)

( * ) Notice: Subject to any disclaimer, the term of this patent is extended or adjusted under 35 U.S.C. 154(b) by 371 days.

(21) Appl. No.: 14/657,678

(22) Filed: Mar. 13, 2015

(65) Prior Publication Data
US 2015/0257643 A1    Sep. 17, 2015

Related U.S. Application Data

(60) Provisional application No. 61/954,075, filed on Mar. 17, 2014.

(51) Int. Cl.
*A61B 5/00* (2006.01)
*A61B 5/1455* (2006.01)
(Continued)

(52) U.S. Cl.
CPC ........ *A61B 5/0002* (2013.01); *A61B 5/02433* (2013.01); *A61B 5/02438* (2013.01);
(Continued)

(58) Field of Classification Search
CPC ............ A61B 5/14552; A61B 5/02438; A61B 5/14551; A61B 5/0205; A61B 5/0002;
(Continued)

(56) References Cited

U.S. PATENT DOCUMENTS 6,470,200 B2    10/2002   Walker et al.
6,816,266 B2    11/2004   Varshneya et al.
(Continued)

FOREIGN PATENT DOCUMENTS

WO    2006079862 A2    8/2006

OTHER PUBLICATIONS

Faisst, Karin, et al.; "Intrapartum Reflectance Pulse Oximetry: Effects of Sensor Location and Fixation Duration on Oxygen Saturation Readings," Journal of Clinical Monitoring, vol. 13, pp. 299-302 (1997).
(Continued)

*Primary Examiner* — Michael Carey
*Assistant Examiner* — Natasha Patel

(57) ABSTRACT

Systems and method for utilizing energy harvesting techniques to power a battery-less wireless medical sensor to perform intermittent operations are disclosed. The systems may include one or more sensing components configured to generate data related to one or more physiological parameters by performing intermittent measurements on a patient. The systems and method may include wireless communication circuitry configured to wirelessly transmit the data to a monitor. The monitor may be configured to operate with the battery-less wireless medical sensor or may download required operational algorithms if needed. The intermittent measurement and transmission may be asynchronously executed. The systems and method may include a processing device configured to determine when to perform the intermittent measurement and transmit data based at least upon a power source energy level, a rate at which to perform the intermittent measurement and transmit data, a prioritization, or a triggering event.

20 Claims, 9 Drawing Sheets

(51) Int. Cl.

| | |
|---|---|
| *A61B 5/024* | (2006.01) |
| *H04W 52/02* | (2009.01) |
| *A61B 5/08* | (2006.01) |
| *A61B 5/0205* | (2006.01) |
| *A61B 5/11* | (2006.01) |
| *H04B 5/00* | (2006.01) |

(52) U.S. Cl.
CPC ........ *A61B 5/14552* (2013.01); *A61B 5/7285* (2013.01); *H04W 52/0216* (2013.01); *H04W 52/0251* (2013.01); *H04W 52/0261* (2013.01); *A61B 5/02055* (2013.01); *A61B 5/0816* (2013.01); *A61B 5/11* (2013.01); *A61B 5/6814* (2013.01); *A61B 5/6816* (2013.01); *A61B 5/6826* (2013.01); *A61B 5/746* (2013.01); *A61B 2560/029* (2013.01); *A61B 2560/0214* (2013.01); *A61B 2562/08* (2013.01); *H04B 5/0037* (2013.01); *H04W 52/0254* (2013.01); *H04W 52/0258* (2013.01); *Y02B 60/50* (2013.01)

(58) Field of Classification Search
CPC ......... H04W 52/0216; H04W 52/0251; H04W 52/0261; A61N 1/3708; A61N 1/37276
See application file for complete search history.

(56) References Cited

U.S. PATENT DOCUMENTS

| | | | |
|---|---|---|---|
| 6,934,571 | B2 | 8/2005 | Weismann et al. |
| 7,209,775 | B2 | 4/2007 | Bae et al. |
| 7,486,977 | B2 | 2/2009 | Sweitzer et al. |
| 7,499,739 | B2 | 3/2009 | Sweitzer et al. |
| 7,658,716 | B2 | 2/2010 | Banet et al. |
| 7,729,733 | B2 | 6/2010 | Al-Ali et al. |
| 7,844,314 | B2 | 11/2010 | Al-Ali |
| 8,133,176 | B2 | 3/2012 | Porges et al. |
| 8,652,040 | B2 | 2/2014 | LeBoeuf et al. |
| 8,742,623 | B1 * | 6/2014 | Biederman .......... G02B 27/017 307/80 |
| 2006/0069319 | A1 | 3/2006 | Elhag et al. |
| 2006/0079794 | A1 | 4/2006 | Liu et al. |
| 2006/0100530 | A1 * | 5/2006 | Kliot .................... A61B 5/0002 600/483 |
| 2006/0253010 | A1 | 11/2006 | Brady et al. |
| 2007/0106132 | A1 | 5/2007 | Elhag et al. |
| 2008/0064936 | A1 * | 3/2008 | Al-Ali ................. A61B 5/1455 600/300 |
| 2009/0281433 | A1 * | 11/2009 | Saadat .............. A61M 5/14244 600/483 |
| 2010/0179389 | A1 * | 7/2010 | Moroney, III ...... G06F 19/3406 600/301 |
| 2011/0208010 | A1 * | 8/2011 | McKenna .......... A61B 5/14551 600/300 |
| 2012/0050038 | A1 * | 3/2012 | Stetter ................. A61B 5/0205 340/540 |

OTHER PUBLICATIONS

Izumi, Akio, et al.; "Accuracy and Utility of a New Reflectance Pulse Oximeter for Fetal Monitoring During Labor," Journal of Clinical Monitoring, vol. 13, pp. 103-108 (1997).
"Smaller Product, Tighter Tolerances Pose Dispensing Challenges for Medical Device Manufacturer," Adhesives Age, pp. 40-41 (Oct. 1997).
Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.
DeKock, Marc; "Pulse Oximetry Probe Adhesive Disks: a Potential for Infant Aspiration," Anesthesiology, vol. 89, pp. 1603-1604 (1998).
Odagiri, Y.; "Pulse Wave Measuring Device," Micromechatronics, vol. 42, No. 3, pp. 6-11 (published Sep. 1998) (Article in Japanese—contains English summary of article).
Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, 1998, vol. 20, No. 4, pp. 1906-1919.
Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.
Such, Hans Olaf; "Optoelectronic Non-invasive Vascular Diagnostics Using multiple Wavelength and Imaging Approach," Dissertation, (1998).
Lutter, N., et al.; "Comparison of Different Evaluation Methods for a Multi-wavelength Pulse Oximeter," Biomedizinische Technik, vol. 43, (1998).
Ferrell, T.L., et al.; "Medical Telesensors," SPIE, vol. 3253, pp. 193-198 (1998).
Yang, Boo-Ho, et al.; "Development of the ring sensor for healthcare automation," Robotics and Autonomous Systems, vol. 30, pp. 273-281 (2000).
Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.
Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796.
Schulz, Christian Eric; "Design of a Pulse Oximetry Sensor Housing Assembly," California State University Master's Thesis, UMI Dissertation Services, UMI No. 1401306, (May 2000) 63 pages.
Aoyagi, T., et al.; "Pulse Oximeters: background, present and future," Neonatal Care, vol. 13, No. 7, pp. 21-27 (2000) (Article in Japanese—contains English summary of article).
Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.
Gisiger, P.A., et al.; "OxiCarbo®, a single sensor for the non-invasive measurement of arterial oxygen saturation and CO2 partial pressure at the ear lobe," Sensor and Actuators, vol. B-76, pp. 527-530 (2001).
Cysewska-Sobusaik, Anna; "Metrological Problems With noninvasive Transillumination of Living Tissues," Proceedings of SPIE, vol. 4515, pp. 15-24 (2001).
Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).
Earthrowl-Gould, T., et al.; "Chest and abdominal surface motion measurement for continuous monitoring of respiratory function," Proc. Instn Mech Engrs, V215, Part H; pp. 515-520 (2001).
Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.
Irie, A., et al.; "Respiration Monitors—Pulse Oximeters," Neonatal Care, vol. 15, No. 12, pp. 78-83 (2002) (Article in Japanese—contains English summary of article).
Shaltis, Phillip, et al.; "Implementation and Validation of a Power-Efficient, High-Speed Modulation Design for Wireless Oxygen Saturation Measurement Systems," IEEE, pp. 193-194 (2002).
Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

(56) References Cited

OTHER PUBLICATIONS

Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Mendelson, Y., et al.; "Measurement Site and Photodetector Size Considerations in Optimizing Power Consumption of a Wearable Reflectance Pulse Oximeter," Proceedings of the 25th Annual International conference of the IEEE EMBS, Cancun, Mexico, Sep. 17-21, 2003.

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Lebak, J.W., et al.; "Implementation of a Standards-Based Pulse Oximeter on a Wearable, Embedded Platform," Proceeding of the 25th Annual International Conference of the IEEE EMBS, Cancun, Mexico, Sep. 17-21, 2003; pp. 3196-3198.

Nagl, L., et al.; "Wearable Sensor System for Wireless State-of-Health Determination in Cattle," Proceeding of the 25th Annual International Conference of the IEEE EMBS, Cancun, Mexico, Sep. 17-21, 2003; pp. 3012-3015.

Pujary, C., et al.; "Photodetector Size Considerations in the Design of a Noninvasive Reflectance Pulse Oximeter for Telemedicine Applications," IEEE, pp. 148-149 (2003).

Wendelken, Suzanne, et al.; "The Feasibility of Using a Forehead Reflectance Pulse Oximeter for Automated Remote Triage," IEEE, pp. 180-181 (2004).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Urquhart, C., et al.; "Ear probe pulse oximeters and neonates," Anaesthesia, vol. 60, p. 294 (2005).

Bentley, David J. et al.; "Measure Pressure with Thin Film"; Paper Film & Foil Converter; May 1, 2003.

http://www.cfw.com.my/fujifilm2.htm.

\* cited by examiner

INTERMITTENT OPERATING BATTERY-LESS WIRELESS SENSOR AND PULSE OXIMETER

CROSS REFERENCE TO RELATED APPLICATION

This application claims priority from and the benefit of U.S. Provisional Application Ser. No. 61/954,075, entitled "INTERMITTENT OPERATING BATTERY-LESS WIRELESS SENSOR AND PULSE OXIMETER", filed Mar. 17, 2014, which is hereby incorporated by reference in its entirety.

BACKGROUND

The present disclosure relates generally to medical monitoring devices and, more particularly, to intermittent operating pulse oximeters.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological parameters of their patients. Accordingly, a wide variety of devices have been developed for monitoring physiological parameters. Such devices provide doctors and other healthcare personnel with the information they need to provide the best possible healthcare for their patients. As a result, such monitoring devices have become an indispensable part of modern medicine.

One technique for monitoring certain physiological parameters of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood ($SpO_2$), the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological parameters based upon the absorption or scattering of the light. More specifically, the emitted light is typically selected to be of one or more wavelengths that are absorbed and/or scattered in an amount related to the presence of oxygenated versus de-oxygenated hemoglobin in the blood. The amount of light absorbed and/or scattered may then be used to estimate the amount of oxygen in the tissue using various algorithms.

In certain situations it may be desirable to have a pulse oximeter that is small, lightweight, inexpensive, and that uses batteries to operate. For example, such battery powered monitors may be used when conventional monitors may be too heavy and bulky to be moved from one patient to another or when medical treatment is desired in a remote location and access to a conventional power source may not be available. However, the batteries may be drained fairly quickly in such pulse oximeters and, thus, require frequent replacement.

The same is true for wireless sensors. Wireless sensors may be desirable to check a patient's status without encumbering the patient with an additional wire. Typically, due to the fact that there is not a wire powering the sensors, wireless sensors require conventional or rechargeable batteries to operate. During operation, the batteries may be drained from performing measurements and transmitting the data. Consequently, the conventional batteries may require replacement, and the rechargeable batteries may need to be recharged, which may present a problem when drained in a remote location where a conventional power source is not available.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
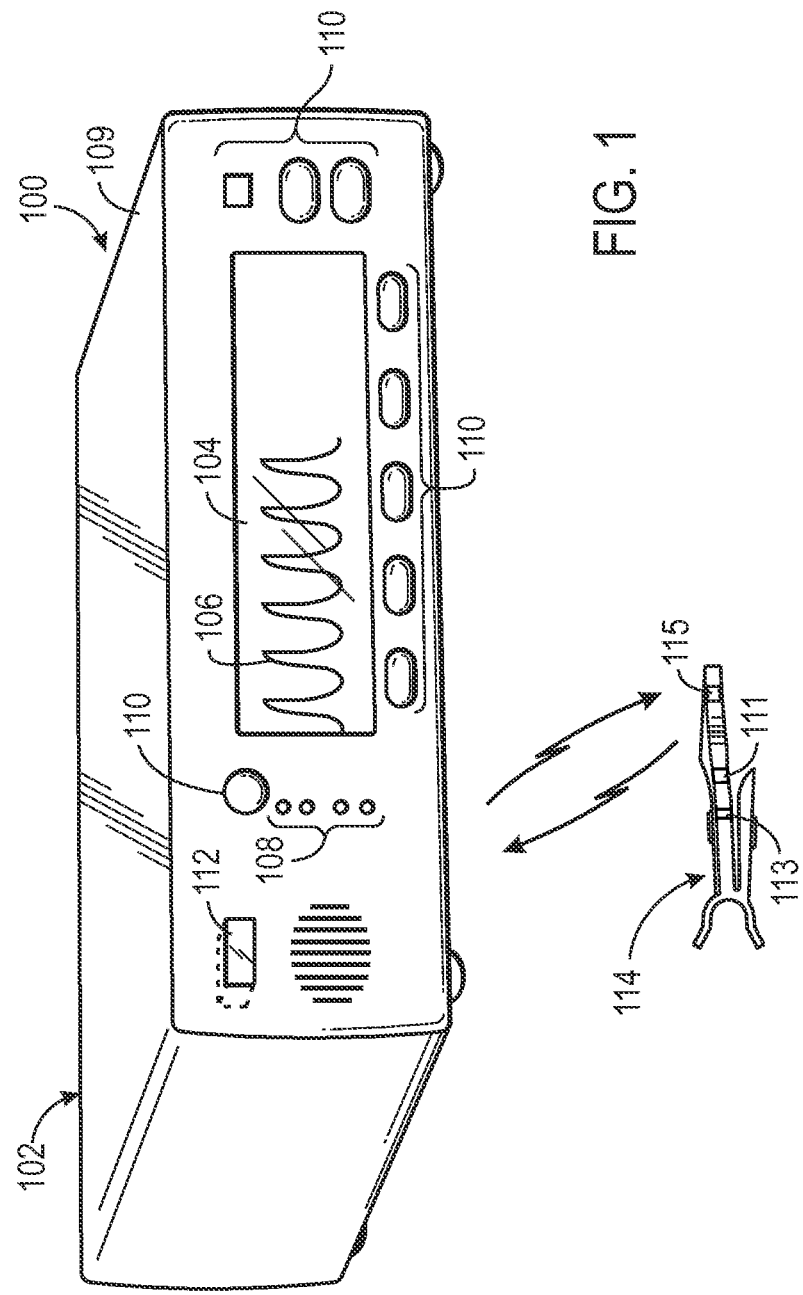
FIG. 1 illustrates a perspective view of a wireless power system including an electronic device, such as a pulse oximeter, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Additionally, it should be noted that the term "reading" and "measurement" may be used interchangeably when referring to the pulse oximeter gathering physiological data herein.

Operating a wireless sensor or monitor over a period of time may drain a power source for the wireless sensor or monitor even if such operation is intermittent. However, using certain methods of power generation, a wireless sensor may recharge itself in order to perform desired intermittent operations, such as taking measurements and/or communicating with external devices. For example, in some embodiments, the energy necessary to power a sensor for an intermittent measurement and/or data transmission may be generated in between each check or transmission. As will be discussed below, the energy may be stored by charging an energy storage component, such as a capacitor or inductor, during the time period between the intermittent measurements and/or data transmissions. This provides the advantage of acquiring the energy required to perform the intermittent measurements and/or data transmission from low grade power sources (i.e. power sources that emit ambient light, heat, and kinetic energy). In particular, various energy harvesting techniques may be utilized that turn ambient light, body heat, body movement, and so forth into energy to charge the power source.

In certain embodiments, the wireless sensor or monitor may determine when to perform a reading or transmit data after the power source has stored a sufficient amount of charge. Indeed, the power source may only have enough energy to either perform a reading or transmit data. Thus, the wireless sensor or monitor may determine to perform an intermittent reading based upon one or more of a power source charge level, a determined measurement rate, a determined measurement priority, or a measurement triggering event. Likewise, the wireless sensor or monitor may determine to intermittently transmit data based upon one or more of the power source charge level, a determined transmission rate, a determined transmission priority, or a transmission triggering event. In this way, the present techniques provide the benefit of the wireless sensor or monitor being capable of dynamically deciding whether to perform a measurement or transmit data based on a number of factors (e.g., battery charge level, patient status, last transmission, etc.). With the foregoing in mind, the present techniques are directed towards medical devices that harvest energy and intermittently operate (e.g., take measurements and transmit data), among other things, as discussed in detail below.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be wireless and powered by batteries, or the monitor 102 may be wired and powered by a conventional power source. In either case, the monitor 102 may be configured to display calculated parameters on a display 104. As may be seen, the display 104 may be integrated into the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 109. The casing 109 may aid in the protection of the internal elements of the monitor 102 from damage.

The monitor 102 may be configured to transmit data wirelessly via a transceiver 112 (e.g., wireless communication circuitry) to another system (not shown), such as a clinician notification system. Additionally, the transceiver 112 may enable for wireless operation signals to be transmitted to and received from a transceiver disposed in a wireless sensor 114. The wireless sensor 114 may be of a disposable or a non-disposable type. The wireless sensor 114 may obtain readings from a patient that can be used by the monitor 102 to calculate certain physiological parameters such as the blood-oxygen saturation of hemoglobin in arterial blood, the volume of individual blood pulsations supplying the tissue, and/or the rate of blood pulsations corresponding to each heartbeat of a patient.

In certain embodiments, the wireless sensor 114 may be powered by a non-battery power source, such as a capacitor or inductor. In other words, the wireless sensor 114 may be battery-less. However, in alternate embodiments the wireless sensor 114 may be powered by a rechargeable battery or conventional battery. As will be discussed in greater detail below, the sensor 114 may include a charging device 115 for harnessing of energy to charge the non-battery power source. The wireless sensor 114 may also include an indicator 111 that may provide an audio or visual indication that the sensor has enough charge to perform an intermittent reading and/or data transmission. The wireless sensor 114 may also include a button/switch 113 that may be pressed in order to trigger the wireless sensor 114 to perform an intermittent reading and/or data transmission to the monitor 102. In some embodiments, once the wireless sensor 114 obtains sufficient charge, it may power on and perform an intermittent measurement and/or transmit data according to a power source charge level, a schedule, a priority, a triggering event, or some combination thereof.

Figure 2:
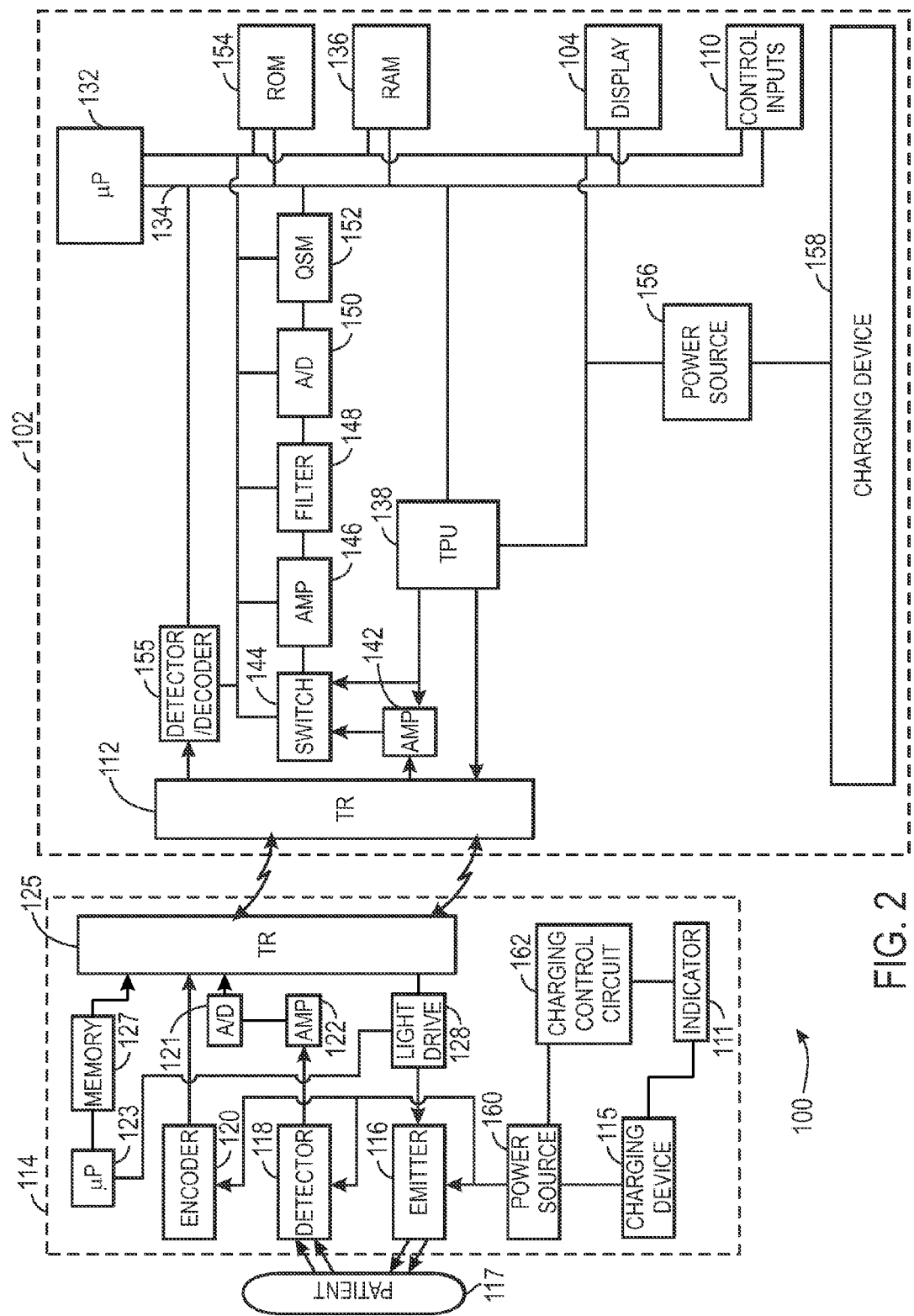
FIG. 2 illustrates a simplified block diagram of the pulse oximeter in FIG. 1, according to an embodiment.

Certain components of the wireless sensor 114 and the monitor 102 included in the pulse oximeter 100 are illustrated in FIG. 2. Oftentimes, the monitor 102 may be placed next to a patient's bed in a hospital room, and the wireless sensor 114 may be attached to a patient's 117 finger, earlobe, and/or forehead. As mentioned, it may be desirable to check a patient's status over a period of time by taking intermittent measurements with the wireless sensor 114 attached to the patient 117. However, the wireless sensor 114 may not always have enough energy to perform both a reading and data transmission. Thus, the wireless sensor 114 may need to be able to recharge itself and determine whether to perform an intermittent measurement and/or transmit data based on a number of factors. To that end, the following description of how the monitor 102 and wireless sensor 114 work together serves as a basis for describing how the wireless sensor harnesses energy and how the monitor 102 and the wireless sensor 114 determine when measurements and/or data transmissions are performed.

In order for the wireless sensor 114 to communicate with the monitor 102, the wireless sensor 114 must identify itself to the monitor 102. This is achieved by the wireless sensor 114 sending information stored on an encoder 120 from transceiver 125 to transceiver 112 when the wireless sensor 114 is first powered on. The encoder 120 may, for instance, be a memory on which one or more of the following information may be stored for communication to the monitor 102: the type of the sensor 114 (e.g., wireless or wired); the wavelengths of light emitted by an emitter 116; the proper calibration coefficients and/or algorithms to be used for calculating the patient's 117 physiological parameters; and/or information regarding a charging device 115 for the wireless sensor 114. For example, the information regarding the charging device 115 may be obtained from a charging control circuit 162 and include information relating to the amount of charge available in a power source 160, the amount of energy required to perform a reading and/or a transmission, the types of suitable charging devices 115 (e.g., kinetic energy harvesting devices, thermoelectric energy harvesting devices, ambient light harvesting devices, etc.), the proper charging of the power source 160 (e.g., which energy harvesting method is preferred), the type of power source 160 utilized by the wireless sensor 114 (e.g., capacitor, inductor, rechargeable battery, etc.), the length of time required to fully charge the power source 160, whether the power source 160 is charging, and so forth.

The charging information may be particularly important in certain embodiments where a capacitor or inductor is utilized by the wireless sensor 114 because it may aid the monitor 102 in determining when to request measurements or transmissions. For example, if the monitor 102 is aware that the wireless sensor 114 is utilizing a capacitor charged by energy harvesting techniques, the monitor 102 may determine a reading or transmission schedule according to how long it takes a capacitor to charge by harvesting energy in those circumstances. In addition, if the monitor 102 is aware of the amount of charge available in the wireless sensor 114 and how much energy is drained from the wireless sensor's 114 power source 160 by performing a measurement and/or a transmission, the monitor 102 may determine that there is a sufficient amount of energy to perform only a measurement or a transmission and request accordingly.

Further, the monitor 102 may be capable of downloading software updates required to operate with the type of battery-less wireless sensor 114 as needed. In some embodiments, the monitor 102 may already have the information needed to operate with the type of battery-less wireless sensor 114 with which it is communicating. That is, if the battery-less wireless sensor 114 is utilizing a capacitor, the monitor 102 may have the operational algorithms required to determine when to request readings and/or data transmissions. An example of an operation algorithm includes determining when to issue a request for data transmission to the wireless sensor 114 based on the type of power source 160 utilized by the sensor 114, the type of energy harvesting technique used, and the amount of charge currently available in the power source 160. However, in other embodiments, the monitor 102 may download the information, such as the operational algorithms, required to operate with the type of battery-less wireless sensor 114 from an external source. In this way, the monitor 102 may be reprogrammable.

After the monitor 102 receives the identifying information from the wireless sensor 114, a detector/decoder 155 disposed in the monitor 102 may decode the information and relay it to the microprocessor 132, which may make several configurations based on the information. For example, the microprocessor 132 may select calibration coefficients for use in algorithms for determining physiological parameters when physiological data is eventually received from the wireless sensor 114, determine an intermittent measurement and/or data transmission schedule for the wireless sensor 114, and so forth.

Once the intermittent measurement schedule is established, the microprocessor 132 may request a measurement to be taken by the wireless sensor 114 at a specified time. To achieve this, the microprocessor 132 may be coupled to an internal bus 134 that is also connected to a time processing unit (TPU) 138. The TPU 138 may provide timing control signals to the wireless sensor's 114 light drive circuitry 128 (e.g., via the transceivers 112 and 125), which controls when an emitter 116 is activated, and if multiple light sources are used, the multiplexed timing for the different light sources. TPU 138 may also control the gating-in of signals from a detector 118 through an amplifier 142 and a switching circuit 144. The amplifier 142 may amplify, for example, the signals from the detector 118 received at the transceiver 112. The TPU 138 may control the gating-in of signals to insure that the signals are sampled at the proper time, which may depend at least in part upon which of multiple light sources is activated, if multiple light sources are used. Likewise, once the transmission schedule is established, the processor 132 may send a request for data transmission to the wireless sensor 114 via transceivers 112 and 125 at a specified time.

In other embodiments, a microprocessor 123 on the wireless sensor 114 may determine when to take an intermittent measurement and/or transmit data based on various factors, which are described in detail below, and send a signal to the light drive circuitry 128 and/or the transceiver 125 accordingly. The microprocessor 123 may make this determination either dynamically or by consulting information (e.g. intermittent measurement schedule, transmission schedule, etc.) in a non-volatile memory 127. Thus, it should be noted that intermittent measurements and/or data transmissions may be triggered by either microprocessors 123 and/or 132. It should be further noted that an intermittent measurement may be random, scheduled to occur at specific intervals, or triggered in response to patient and environmental conditions. In other words, the physiological parameters are not continuously being gathered by the wireless sensor 114. If an intermittent reading is triggered, the light drive circuitry 128 will receive a signal from the microprocessor 123 or the transceiver 125 and it will activate the emitter 116.

The emitter 116 may be capable of emitting at least two wavelengths of light, e.g., RED and infrared (IR) light, into the tissue of the patient 117 to enable calculation of the patient's 117 physiological parameters, such as blood oxygen saturation, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 118 may be capable of detecting certain wavelengths of light. In another example, the detector 118 may detect a wide spectrum of wavelengths of light, and the monitor 102 may process only those wavelengths which are of interest for use in measuring, for example, blood oxygen saturation, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

The detector 118 may generate electrical signals (e.g., analog) in response to the total light detected from the emitter 116, i.e., light that has passed through the patient's 117 tissue and shunted light. However, due to attenuation from passing through the patient's 117 tissue, the received electrical signals may be amplified by an amplifier 122. The signals may then be converted to digital signals by an analog-to-digital converter 121 and sent to the monitor 102 via transceivers 125 and 112. In an embodiment, if the power source 160 lacks sufficient charge to transmit the data, the data may be stored in the non-volatile memory 127 until sufficient charge to transmit is obtained. Therefore, the physiological data collection and the data transmission may be asynchronous because they do not need to occur at the same time. As an example, the intermittent measurement and the wireless transmission of the collected data may be separated by a time period sufficient to recharge the power source 160.

Once transmitted to the monitor 102, if for some reason the signals received require further amplification and/or digitization, i.e., there are multiple light wavelengths or spectra received, the received signals from the detector 118 may be passed through an (optional) amplifier 146, a low pass filter 148, and an analog-to-digital converter 150 for amplifying, filtering, and digitizing the electrical signals from the wireless sensor 114. The digital data may then be stored in a queued serial module (QSM) 152, for later downloading to RAM 136, which is also connected to the internal bus 134 along with a display 104 and control inputs 110.

In other embodiments, the received signals may be sent to the detector/decoder 155 that may select the appropriate calibration coefficients according to signals received from encoder 120, which may correspond to the wavelengths of light used by the wireless sensor 114. The received signals, along with the appropriate calibration coefficients, may be sent to the microprocessor 132. The microprocessor 132 may use the coefficients provided by the detector/decoder 155 or that were determined earlier when the wireless sensor 114 first identified itself to determine attenuation of the tissue of interest. Once the attenuation of the tissue of interest is calculated, it may be used in computing physiological parameters, such as blood oxygen saturation, using various algorithms. The algorithms may be stored in a ROM 154 and accessed and operated according to microprocessor 132 instructions. The monitor 102 may also include a power source 156 that may be used to transmit power to the components located in the monitor 102. In one embodiment, the power source 156 may be one or more batteries, such as a rechargeable battery. The battery may be user-removable or may be secured within the housing of the monitor 102. Use of a battery may, for example, enable the oximeter 100 to be highly portable, thus allowing a clinician to carry and use the oximeter 100 in a variety of situations and locations. Additionally, the power source 156 may include AC power, such as provided by an electrical outlet, and the power source 156 may be connected to the AC power via a power adapter through a power cord (not shown). This power adapter may also be used to directly recharge one or more batteries of the power source 156 and/or to power the pulse oximeter 100. In this manner, the power adapter may operate as a charging device 158.

The wireless sensor 114 may also include the charging control circuit 162, which may, for example, allow for the adaptive control of wireless energy harvested from the charging device 115 for use in the power source 160. The charging control circuit 162 may, for example, include a processing circuit that may determine the current level of charge remaining in the power source 160, as well as the current amount of power being harvested by the charging device 115. For example, the charging control circuit 162 may determine if the charging device 115 is generating too little power to charge the power source 160. In response to determining that the charging device 115 is generating too little power to charge the power source 160 and that the power source 160 is low on power, the charging control circuit 162 may generate an error signal that may be transmitted to the monitor 102 via the transceivers 125 and 112.

In response to the error signal, the monitor 102 may (e.g., via the processor 132) display an error on the display 104 of the monitor 102. The error message may indicate to a clinician that the sensor 114 is low on power and may also direct the clinician to take action, such as changing the power source 160 (e.g., installing new batteries), charging the power source 160 (i.e. by shining a light on the sensor 114, plugging the sensor 114 into a charging unit or into an electrical outlet via a power adapter, having the patient 117 to which the sensor 114 is attached move, etc.). Alternatively, the error message may indicate to a clinician that the recharging system of the sensor 114 is potentially malfunctioning, and may direct the clinician, for example, to replace the wireless sensor 114. In an embodiment, the error message may be generated when the charging control circuit 162 determines that the power source 160 has reached a certain charge level, for example, 20% of the total charge remains in the power source 160. Additionally, as described below in greater detail, the charging control circuit 162 may also include conversion translation circuitry, such as a rectifier circuit, for conversion of alternating current generated via the charging device 115 into direct current.

In other embodiments, in response to determining that the charging device 115 is generating too little power to charge the power source 160 and that the power source 160 is low on power, the charging control circuit 162 may generate an error signal that may be displayed by an indicator 111 on the wireless sensor 114. The indicator may provide audio or visual indications by means of a sound or a color that indicates an error has occurred. The error indication may provide the same warnings as discussed above. Alternatively, when the power source 160 has received sufficient charge to perform an intermittent measurement or transmit data, the charging control circuit 162 may generate a signal to the indicator 111 to indicate that the sensor 114 has enough energy to perform the intermittent measurement or data transmission. As a result, the indicator 111 may display a visual indication, such as a green light or any suitable color, or emit an audio indication that the power source 160 has a sufficient charge.

Furthermore, the charging device 115 may be one of a multitude of energy harvesting components that utilize, for example, inductive energy generation techniques and/or piezoelectric energy generation techniques. Through the use of these techniques, energy may be harvested, for example, through motion of a patient 117, body heat of a patient 117, and/or ambient light, and utilized to directly recharge the power source 160 within the sensor 114.

Figure 3:
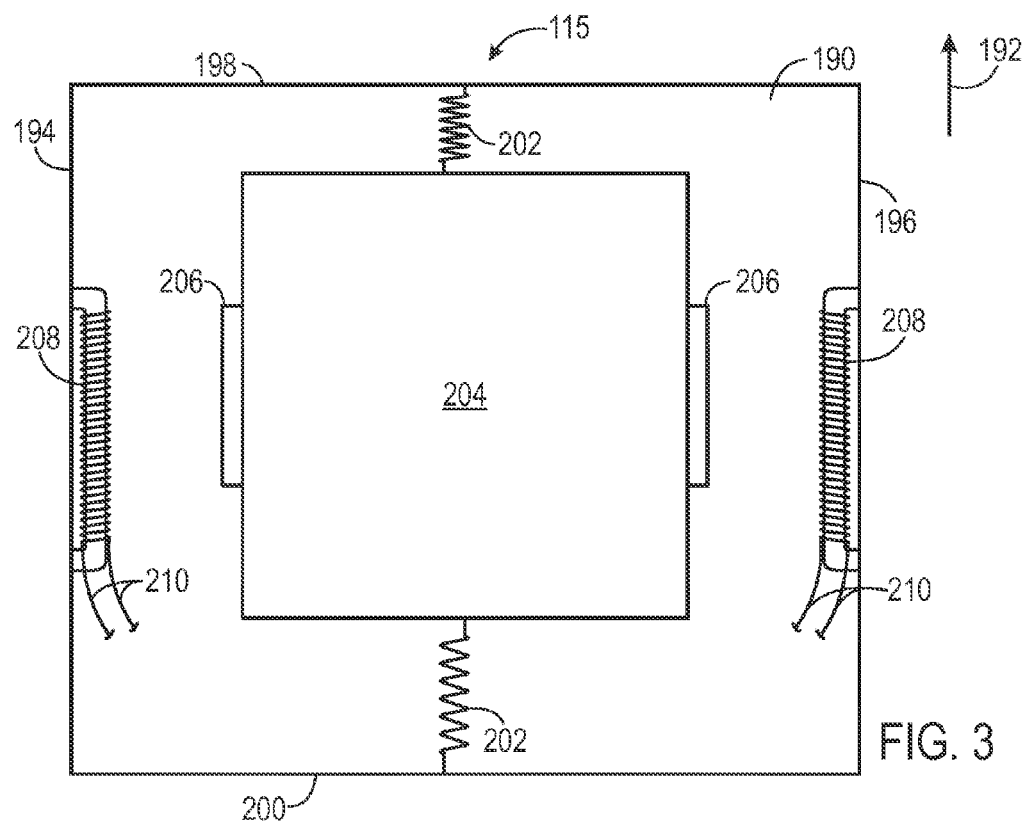
FIG. 3 illustrates the charging device of FIG. 1 (e.g., utilizing kinetic energy harvesting), in accordance with an embodiment.

For example, an embodiment of a charging device that utilizes kinetic energy harvesting techniques is illustrated in FIG. 3. The charging device 115 may include an energy harvester 190 that may convert vibratory motion along an axis 192 into electrical energy. One or more energy harvesters 190 may be utilized in conjunction with one another and the energy harvester 190 may be sized to be imbedded in the sensor 114 or attached thereto as microelectromechanical systems (MEMS), nanoelectromechanical systems (NEMS), or as other systems. The energy harvester 190 may be enclosed by, for example, four partitions 194, 196, 198, and 200. As may be seen, partitions 194 and 196 may be opposite paired partitions while partitions 198 and 200 may also be opposite paired partitions. The energy harvester 190 may further include one or more attachment devices, such as springs 202, which may be utilized to suspend enclosure 204 from partitions 198 and 200. The springs 202 may enable for reciprocating movement of the enclosure 204 relative to partitions 194 and 196 only along the axis 192. This movement of the enclosure 204 may be in response to movement by the patient 117.

Additionally, the enclosure 204 of the energy harvester 190 may include one or more magnets 206 attached thereto. Accordingly, the enclosure 204, may enable for reciprocating movement of the magnets 206 relative to the partitions 194 and 196. Indeed, one or more coils 208 may be attached to the partitions 194 and 196 such that the reciprocating movement of the magnets 206 inductively generates a current in the coils 208. This induced current in coils 208 may be transmitted via conductive leads 210 to the charging control circuit 162 or directly to the power source 160. As noted above, the current generated may pass through a rectifier circuit, a transformer, or a phase converter as, for example, part of the charging control circuit 162. Accordingly, the energy harvester 190 may convert input kinetic energy, for example, movement by the patient 117 causing reciprocating movement of the enclosure 204 (and thus the magnets 206 attached thereto), into electricity useable by the pulse oximeter 100.

Figure 4:
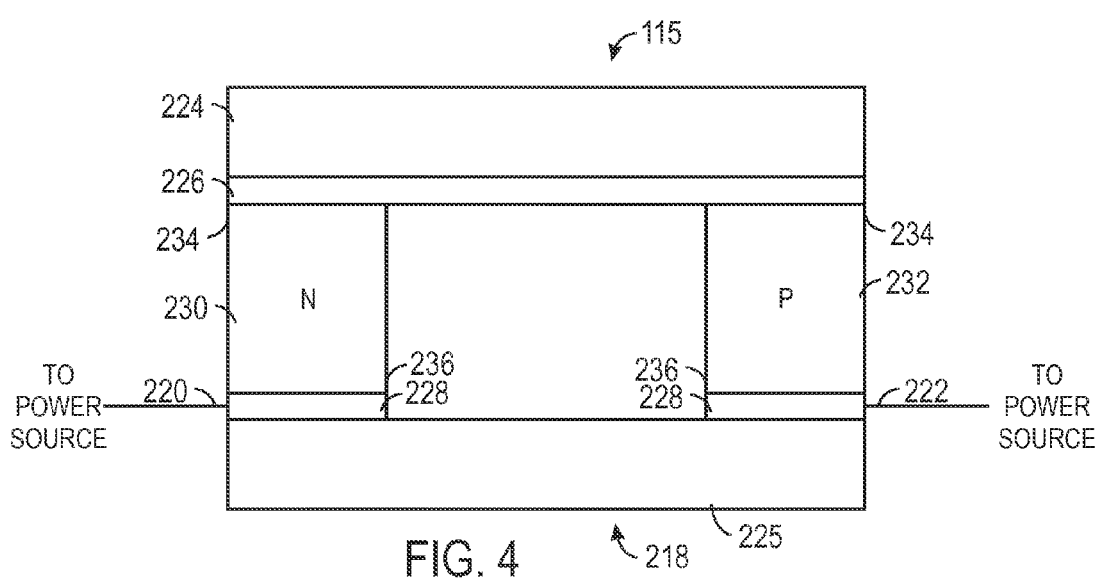
FIG. 4 illustrates the charging device of FIG. 1 (e.g., utilizing thermoelectric energy harvesting), in accordance with an embodiment.

Additionally, FIG. 4 illustrates another example of the charging device 115 of FIG. 1. In this embodiment, the charging device 115 utilizes thermoelectric energy harvesting techniques. The thermoelectric energy harvester 218 may include one or more substrate layers 224 and 225, conductive layers 226 and 228, and one or more thermoelectric materials 230 and 232. Also included are leads 220 and 222 coupled to the thermoelectric energy harvester 218. Substrate layers 224 and 225 may include a ceramic, aluminum nitride (AlN), alumina ($Al_2O_3$), $SiO_2$, or any other electrically insulating and thermally conducting material. The substrate layers 224 and 225 may be, for example, approximately between 100 and 2000 micrometers ($\mu m$) in thickness. Coupled to each of the substrate layers 224 and 225 is conductive layer 226 and 228, respectively. These conductive layers 226 and 228 may include gold, aluminum, copper, or any other electrically conductive material. The conductive layers 226 and 228 may be, for example, approximately between 25 and 500 $\mu m$ in thickness. As illustrated, leads 220 and 222 may be attached to one of the conductive layers, for example, layer 228. Additionally coupled to each of the conductive layers 226 and 228 are thermoelectric materials 230 and 232. As illustrated, the thermoelectric materials 230 and 232 are electrically coupled in series and thermally coupled in parallel. The thermoelectric materials 230 and 232 may be, for example, approximately between 1000 and 10,000 $\mu m$ in thickness and may also be semiconductors.

For example, thermoelectric material 230 may include bismuth telluride ($Bi_2Te_3$), lead telluride (PbTe), cobalt triantimonide ($CoSb_3$), Silicon-germanium (SiGe), or $La_3Te_4$. The thermoelectric material 230 may also be doped by introducing impurities into the thermoelectric material 230 to change its electrical properties, in this case, to introduce an impurity with a surplus of electrons to generate an N-type thermoelectric material. Thermoelectric material 232 may include $SbTe_3$, PbTe, SiGe, $CeFe_4Sb_{12}$, or $Yb_{14}MnSb_{11}$. The thermoelectric material 232 may also be doped by introducing an impurity with a surplus of free charge carriers (holes) to generate a P-type thermoelectric material.

As illustrated, the thermoelectric energy harvester 218 may generate electricity in the presence of temperature differences between substrate layers 224 and 225. For example, substrate layers 224 and 225 may be coupled to interface layers. Furthermore, a heat source, such as the skin of a patient 117, may be adjacent to substrate layer 224, while a heat sink, such as the ambient air surrounding a patient 117, may be adjacent to substrate layer 225. Accordingly, because substrate layers 224 and 225 are thermally conductive, a temperature difference may be experienced at the upper portion 234 and the lower portion 236 of the thermoelectric materials 230 and 232.

In thermoelectric material 230, free electrons may carry both charge and heat. Similarly, in thermoelectric material 232, holes may carry both charge and heat. Thus, when the portions 234 and 236 of thermoelectric materials 230 and 232 are exposed to different temperatures, free electrons in thermoelectric material 230 may flow from the heated portion 234 of thermoelectric material 230 to the cooler portion 236 of thermoelectric material 230. This may generate a positive charge at the upper portion 234 and a negative charge at the lower portion 236 of thermoelectric material 230. Simultaneously, holes in thermoelectric material 232 may flow from the heated portion 234 of thermoelectric material 232 to the cooler portion 236 of thermoelectric material 232, creating a positive charge at the upper portion 234 and a negative charge at the lower portion 236 of thermoelectric material 232. Furthermore, by connecting conductive layer 226 between the upper portion 234 of the thermoelectric materials 230 and 232, and by connecting leads 220 and 222 to the lower portion 236 of the thermoelectric materials 230 and 232 (as well as to the power source 160), a circuit may be completed (closed). Closure of this circuit may enable for the flow of current through the thermoelectric energy harvester 218 to the power source 160 for charging of the power source 160 and/or powering of the sensor 114.

In other embodiments, a clinician could carry a means to power the wireless sensor 114 that harvests energy from ambient light. For example, the clinician may carry a light which the clinician may shine on the sensor 114. The sensor may utilize energy harvesting techniques to convert the light into energy and power the sensor 114 when a sufficient amount of energy has been stored by the power source 160. Alternatively, an inducting loop, or power lead from a carried battery may also be employed to power the sensor 114.

Figure 5:
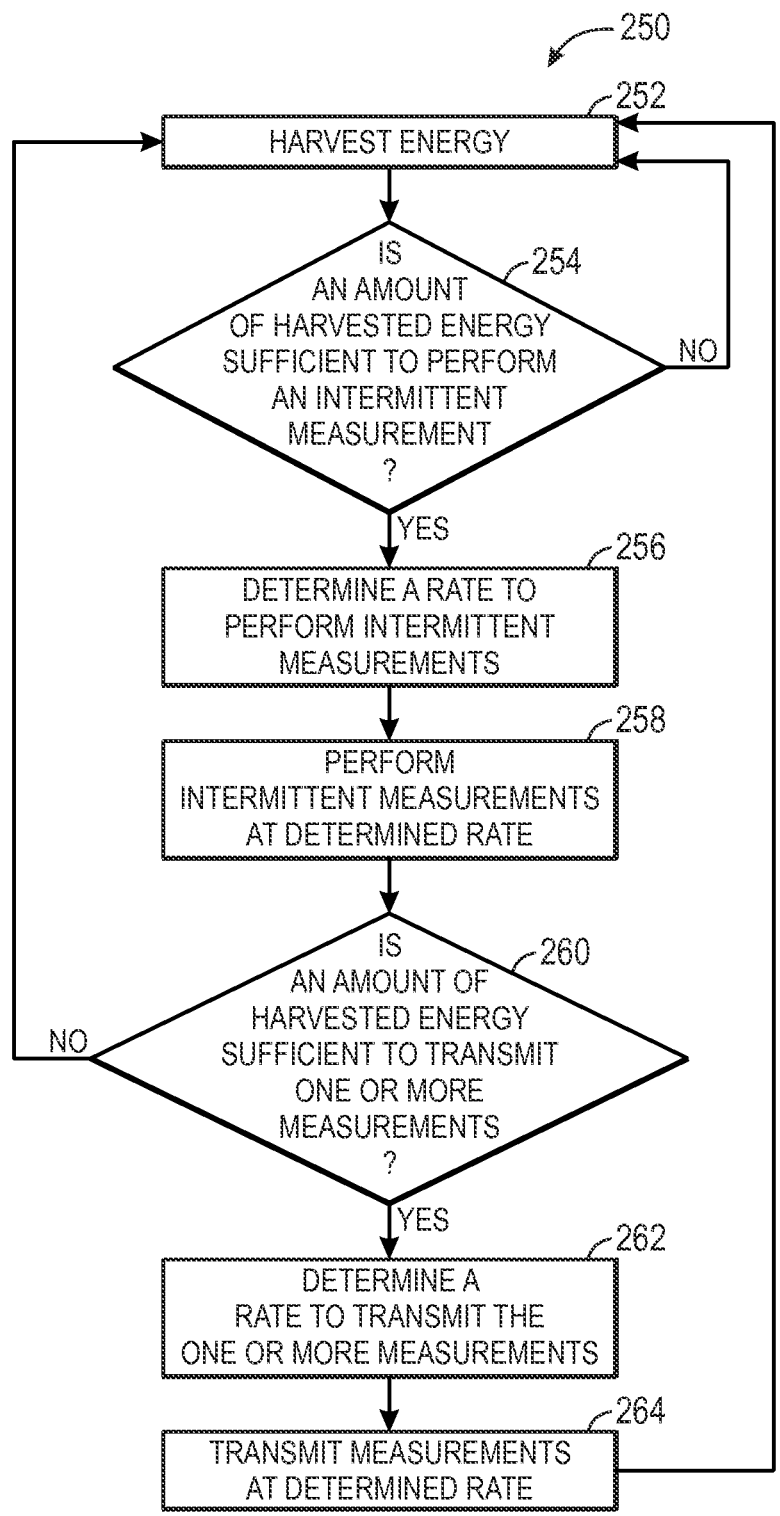
FIG. 5 is a flowchart describing an embodiment of a method for utilizing energy harvesting to perform intermittent operations based upon charge level and determined rates.

Whichever energy harvesting technique is utilized, FIG. 5 depicts a flowchart describing an embodiment of a method 250 for utilizing the energy harvesting technique to perform intermittent measurements and data transmissions. As such, the method 250 depicted begins with step 252 where the charging device 115 in the sensor 114 is harvesting energy. In step 254, the charging control circuit 162 determines a power source energy level of the power source 160 and microprocessor 123 or 132 determines whether the power source 160 energy level (e.g., amount of harvested energy)

is sufficient to perform an intermittent measurement or to wirelessly transmit measurement data. If microprocessor 123 or 132 determines that the amount of harvested energy is not sufficient to perform an intermittent measurement, the method 250 returns to step 252 to continue harvesting energy. However, if microprocessor 123 or 132 determines that the amount of harvested energy is sufficient to perform an intermittent measurement, then microprocessor 123 or 132 determines a rate for performing intermittent measurements in step 256.

As discussed above, if microprocessor 123 or 132 determines that there is or is not enough charge to perform the intermittent measurement, it may send a signal to the indicator 111 to provide a visual and/or audio indication reflecting as such. In certain embodiments, microprocessor 123 may access the non-volatile memory 127 where a predetermined rate for intermittent readings has been stored. In another embodiment, the microprocessor 123 may send a control signal to the transceiver 125 to communicate with the monitor 102 to obtain an intermittent reading rate from microprocessor 132. As a result, the monitor 102 may send an intermittent reading rate to the sensor 114 via transceivers 112 and 125, which the sensor 114 may then store in the non-volatile memory 127. In yet another embodiment, the microprocessor 123 may determine the intermittent reading rate dynamically without consulting the non-volatile memory 127 or the monitor 102. The microprocessor 123 may consider several factors when determining the intermittent reading rate. Some factors may be similar to the factors for determining the intermittent measurement priority and may include when the last reading was performed, the health of the patient 117, previous measurements, and so forth (see FIG. 8).

After the rate for performing intermittent readings is determined in step 256, microprocessor 123 or 132 may send control signals to the light drive circuitry 128 to activate the emitter 116 and perform intermittent readings according to the determined rate as indicated in step 258. Optionally, in step 256, the microprocessor 123 may store the determined intermittent reading rate in the non-volatile memory 127 for later use. It should be noted that at any time, the clinician may press the button/switch 113 on the sensor 114 to perform a reading, assuming that the sensor 114 has sufficient charge. The intermittent readings may measure any number of targeted physiological parameters including pulse rate, respiration rate, blood oxygen saturation, patient temperature, and so forth. In step 260, the charging control circuit 162 may determine the power source 160 energy level (e.g., amount of harvested energy) and the microprocessor 123 or 132 may determine whether the power source energy level is sufficient to transmit one or more measurements and/or other data (e.g. amount of charge, and others which will be discussed in detail below). As previously mentioned, in some embodiments, if there is not enough energy to transmit the measurements and/or data to an external device, such as the monitor 102, the measurements taken during the reading may be stored in the non-volatile memory 127. Alternatively, if there is sufficient energy stored in the power source 160 to transmit, the microprocessor 123 or 132 may determine a rate at which to transmit the one or more measurements and other data, as shown in step 262.

The transmission rate and the intermittent reading rate may vary, meaning intermittent readings and transmissions may occur asynchronously. Similar to determining the rate at which intermittent readings may be performed, determining the rate at which reading measurements or other data is to be transmitted may be based on a stored interval in the non-volatile memory 127, provided by the monitor 102, or may be computed dynamically. The microprocessor 123 or 132 may determine the transmission rate dynamically by evaluating one or more update factors, which may represent various criteria for determining an appropriate quantity and rate of data to send to the monitor 102.

For example, the method 250 described by the flowchart may enable determining that a stored energy level is insufficient to transmit a full dataset of data collected by the sensor 114. Thus, the amount of data sent by the sensor 114 to the monitor 102 may be reduced as compared to transmitting all collected measurement data. As a result, the amount of power consumed by transmitting the data may be reduced. This is beneficial when the power source only has a limited charge and may not be able to send the entire dataset from the sensor 114.

Figure 6:
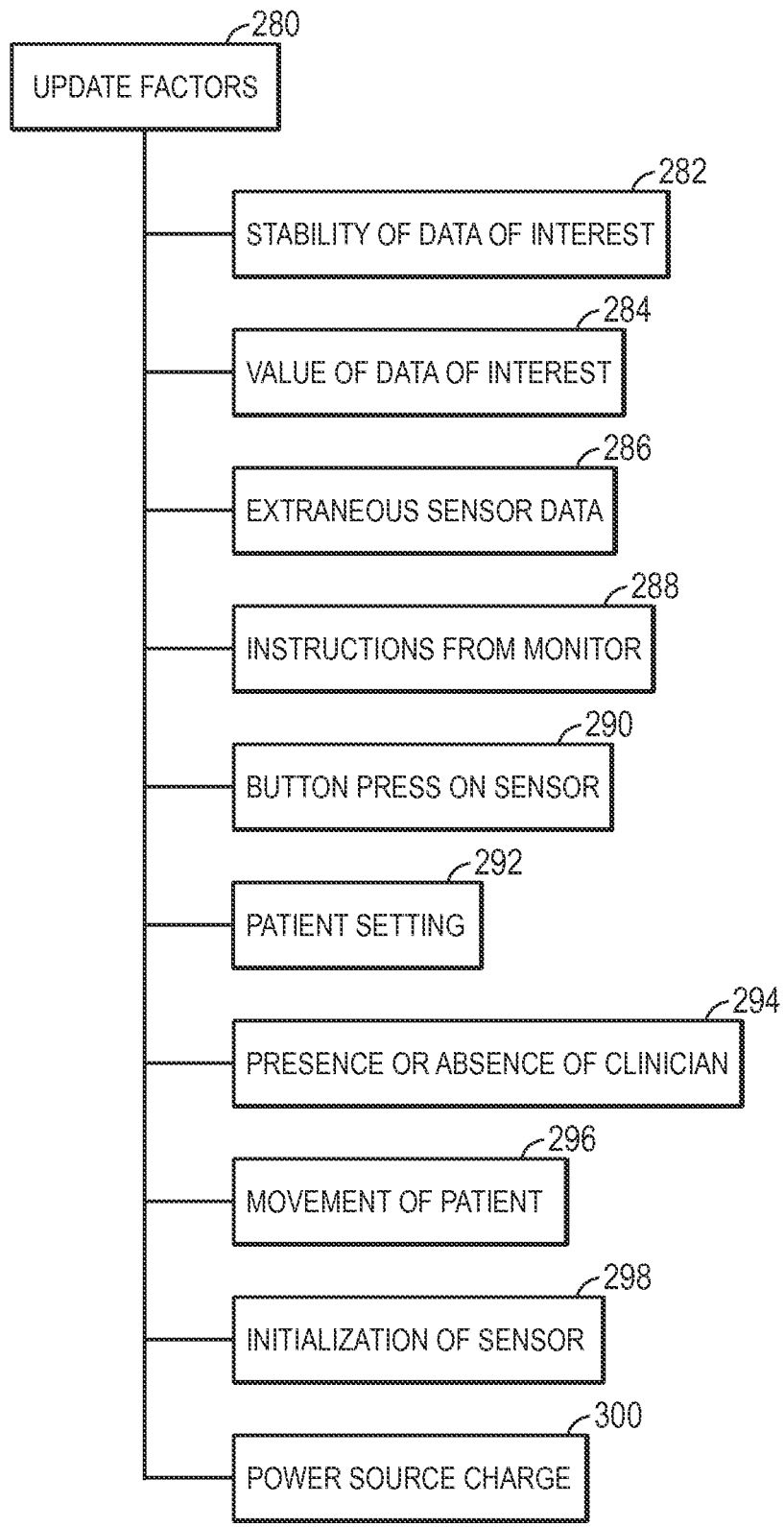
FIG. 6 is a schematic diagram of various factors that may be utilized with the method of FIG. 5, in accordance with an embodiment.

Any number of suitable update factors 280 may be considered, many of which may be described with reference to the schematic diagram depicted in FIG. 6. As should be appreciated, precisely which update factors 280 may be considered by the microprocessor 123 or 132 may be predetermined or may be selected by the microprocessor 123 or 132 based on the current condition of the patient 117 and/or the particular medical application for which the sensor 114 is being used. It should be noted that the terms "update interval" and "transmission rate" are used interchangeably herein.

One factor 282 of the update factors 280 may be the stability of the data of interest obtained by the sensor 114 for a recent historical period. The sensor 114 may extract the data of interest (e.g., pulse rate, blood oxygen saturation, etc.) from a raw stream of data (e.g., a raw 16-bit digital stream of photoplethysmographic data sampled at between approximately 50 Hz or less to 2000 Hz or more (e.g., approximately 1211 Hz)). If the data of interest is within a predetermined variability threshold over a recent historical period (e.g., 5 minutes), the factor 282 may weigh in favor of a relatively longer transmission rate. If the data of interest varies beyond the predetermined variability threshold, the factor 282 may weigh in favor of a relatively shorter update interval. The factor 282 may trigger an immediate update when the data of interest is outside the expected variability, such as if a patient's heart rate suddenly changes from a range of 70-75 bpm to 120 bpm. In determining the update interval based at least in part on the factor 282, the microprocessor 123 or 132 may further consider how much the data of interest has varied. For example, the greater the variability of the data of interest, the more the factor 282 may weigh in favor of a shorter update interval.

A second factor 284 of the update factors 280 may be an absolute value of the data of interest obtained by the sensor 114. If the data of interest is within a predetermined acceptable range of values, the factor 284 may weigh in favor of a comparatively longer update interval. If the data of interest is higher or lower than the predetermined acceptable range of values, the factor 284 may weigh in favor of a comparatively shorter update interval. By way of example, if the data of interest includes a respiration rate, a predetermined acceptable range of values for an adult patient may be a range of 12 to 20 breaths per minute. A respiration rate less than 12 breaths per minute or greater than 20 breaths per minute may be evaluated by the microprocessor 123 or 132 as weighing in favor of a shorter update interval. In determining the update interval based at least in part on the factor 284, the microprocessor 123 or 132 may further consider how much the absolute value of the data of interest varies beyond the predetermined acceptable range. For example, the more the data of interest varies from the predetermined acceptable range, the more the factor 284 may weigh in favor of a shorter update interval.

A third factor 286 of the update factors 280 may be the stability of extraneous sensor data or an absolute value of the extraneous sensor data. Extraneous sensor data may represent data not generally being transmitted as data of interest. By way of example, a current patient temperature may be extraneous sensor data when the data of interest is obtained from a photoplethysmographic measurement (e.g., pulse rate, blood oxygen saturation, etc.). Like the factors 282 and/or 284, if the extraneous sensor data exceeds a predetermined acceptable range of variability over a recent historical period, or if an absolute value of the extraneous sensor data exceeds a predetermined acceptable range of values, the factor 286 may weigh in favor of a shorter update interval. Similarly, if the extraneous sensor data remains within the predetermined acceptable range of variability over the recent historical period, or if the absolute value of the extraneous sensor data does not exceed the predetermined acceptable range of values, the factor 286 may weigh in favor of a longer update interval. By way of example, if the current patient temperature falls outside a predetermined acceptable range of values (e.g., a range of between 97.6° F. and 99.6° F.), the microprocessor 123 or 132 may interpret the factor 286 as weighing in favor of a shorter update interval for photoplethysmographic data of interest. Also like the factors 282 and/or 284, in determining the update interval based at least in part on the factor 286, the microprocessor 123 or 132 may further consider how much the extraneous sensor data has varied over time or how much the absolute value of the extraneous sensor data varies beyond the predetermined acceptable range. For example, the more the extraneous sensor data exceeds the predetermined acceptable range, the more the factor 286 may weigh in favor of a shorter update interval.

Express instructions received by the wireless medical sensor 114 from the patient monitor 102 may constitute a fourth factor 288 of the update factors 280. In the course of wireless communication with the sensor 114, the patient monitor 102 may transmit updates to sensor parameters in an acknowledgement, or ACK, packet. These sensor parameter updates from the patient monitor 102 may instruct the sensor 114 to send data at a particular interval, to send data in a continuous stream of raw data, or may provide other indications, such as a button press on the monitor 102, which may be interrupted by the sensor 114 and used to determine the update interval. To provide one example, by pressing a button on the patient monitor 102, medical personnel may cause the patient monitor 102 to instruct the wireless medical sensor 114 to transmit the raw stream of data.

A fifth factor 290 of the update factors 280 may be a press of the button or switch 113 on the wireless medical sensor 114. If the button or switch 113 is pressed, the factor 290 may weigh in favor of a shorter update interval. For example, by pressing the button or switch 113, the clinician may be requesting updated information at the monitor 102 and the sensor 114 may transmit the data immediately.

A sixth factor 292 of the update factors 280 may be the current location of the patient 117, which may be supplied to the wireless medical sensor 114 via parameter updates from the monitor 102. Because the amount of data from the wireless medical sensor 114 that should be supplied to the patient monitor 102 may vary depending on whether the patient 117 is in surgery, in recovery, or undergoing other tests, the current location of the patient 117 may be considered as one of the update factors 280. Thus, if the patient 117 is currently located in a medical facility room where the patient 117 should be kept under especially close scrutiny, such as an operating room, the factor 292 may weigh in favor of a correspondingly shorter update interval. If the patient 117 is currently located in a medical facility room where the patient 117 may be kept under less scrutiny, such as a recovery room, the factor 292 may weigh in favor of a longer update interval.

In determining the update interval based at least in part on the factor 292, the microprocessor 123 or 132 may give different locations different weights in favor of a shorter or longer update interval. For example, if the current location is a testing room, such as a CT room, or an operating room, the factor 292 may weigh in favor of a comparatively shorter update interval. However, the factor 292 may weigh more heavily in favor of a shorter update interval if the current location of the patient 117 is the operating room. Similarly, the sensor 114 may be instructed to stop transmitting data or use a very long update interval if the patient 117 is located in close proximity to an instrument which is sensitive to wireless interference. In such a case, if the sensor 114 includes frequency hopping capabilities, the sensor 114 may select an alternate frequency or channel which does not interfere with nearby equipment or sensors located on other patients. In this way, data from a critically ill patient or patient in the operating room may be prioritized higher than patients who are relatively stable.

A seventh factor 294 of the update factors 280 may be the presence or the absence of a clinician proximate to the patient 117, which may be supplied to the wireless medical sensor 114 via parameter updates from the patient monitor 102. For example, if a clinician enters a room where the patient 117 is currently located, the factor 294 may weigh in favor of a comparatively shorter update interval. If the clinician exits the room, the factor 294 may weigh in favor of a comparatively longer update interval. In determining the update interval based at least in part on the factor 294, the microprocessor 123 or 132 may weigh the factor 294 more heavily in favor of a shorter or longer update interval based on the number or patient assignment of clinicians present. For example, if a clinician that is not assigned to the patient 117 enters a room where the patient 117 is currently located, the factor 294 may not weigh as heavily in favor of a shorter update interval as when a clinician that is assigned to the patient 117 enters the room.

An eighth factor 296 of the update factors 280 may be the movement of the patient 117, which may be indicated to the wireless medical sensor 114 via parameter updates from the patient monitor 102. Also, if the charging device 115 utilizes kinetic energy harvesting techniques, the charging device 115 may indicate that movement is detected. If the patient 117 is currently moving, indicating that the patient 117 is not at rest or is being moved from one room to another, the factor 296 may weigh in favor of a comparatively shorter update interval. If the patient 117 is not currently moving, the factor 296 may weigh in favor of a comparatively longer update interval. Additionally, the amount of current patient movement may further affect the weight of the factor 296 in favor of a comparatively shorter or longer update interval.

A ninth factor 298 of the update factors 280 may be an initialization status of the sensor 114. For a predetermined period of time while the sensor is being initialized (e.g., 5 minutes), the update rate of the sensor 114 may be temporarily increased dramatically, such that the raw data stream is supplied to the patient monitor 102. By supplying a raw data stream during the initialization of the sensor 114, a clinician for other medical personnel may properly fit the sensor 114 to the patient 117. In this way, the factor 298 may weigh very heavily in favor of a shorter update interval when the sensor 114 has recently been activated.

A tenth factor 300 of the update factors 280 may be an amount of charge the power source 160 has in the wireless medical sensor 114. If the power source 160 of the sensor 114 has more than a predetermined amount of sufficient charge to transmit, the factor 300 may weigh in favor of a comparatively shorter update interval. If the power source 160 has less than the predetermined amount of sufficient charge to transmit, the factor 300 may weigh in favor of a comparatively longer update interval. This factor 300 may also account for the transmit power required to send error-free data at the last update. For instance, when the patient 117 is relatively far from the receiver, more transmit power may be required, so less frequent updates may take place, especially when the power source 160 is low on charge.

Returning to FIG. 5, after the transmission rate or update interval is determined in step 262, the microprocessor 123 may send signals to the transceiver 125 to transmit measurement data and/or other data at the determined rate as depicted in step 264. Optionally, in step 262, the microprocessor 123 may store the determined transmission rate in the non-volatile memory 127 for later use. Upon transmitting the measurement data and/or other data, the sensor 114 may return to step 252 and begin the cycle again by harvesting energy.

Figure 7:
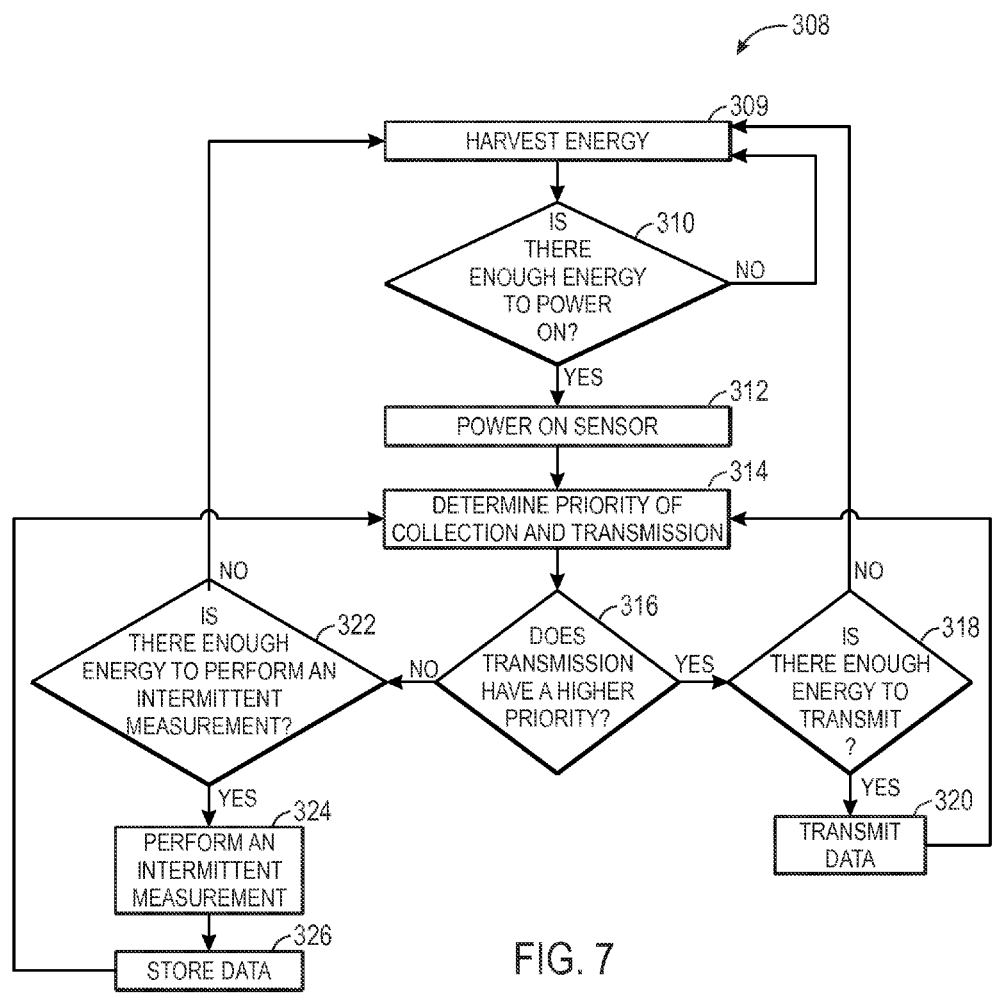
FIG. 7 is a flowchart describing an embodiment of a method for utilizing energy harvesting to perform intermittent operations based upon determined priorities.

Another embodiment of a method 308 for utilizing energy harvesting to perform intermittent measurements and to transmit data is depicted by the flowchart in FIG. 7. The method 308 begins at step 309 by harvesting energy using one of the means discussed above. The harvested energy is used to charge the power source 160 (e.g., energy storage component, such as a capacitor, or inductor, or rechargeable battery). As the charging device 115 is harvesting energy, the charging control circuit 162 may determine a power source 160 energy level (e.g., amount of harvested energy) and the microprocessor 123 may determine whether there is enough energy to power on the sensor 114, as shown in step 310. If there is not enough energy stored to power on the sensor 114, then the charging control circuit 162 may send a signal to the charging device 115 to continue harvesting energy, and the method may return to step 309. However, as seen in step 312, if there is enough energy to power on the sensor 114, then the sensor 114 may power on. Additionally, if there is sufficient energy to perform an intermittent measurement or a data transmission, the charging control circuit 162 may send a signal to the indicator 111 signifying as such. As a result, the indicator 111 may provide an audio and/or visual indication that there is sufficient charge to perform an operation.

Once powered on, the microprocessors 123 or 132 may determine the priority of intermittent measurement collection and data transmission as show in step 314. As previously discussed, the data collection and data transmission may be asynchronous and not occur at the same time. For example, the intermittent measurement and the wireless transmission of the collected data may be separated by a time period sufficient to recharge the power source 160. Since there may only be enough energy stored in the power source 160 to perform either the intermittent measurement or data transmission, the priority of each may be determined by the sensor 114 or monitor 102 to decide which action to execute. Priority of the intermittent measurement and the transmission may be computed dynamically by the microprocessor 123 or 132. In one embodiment, the microprocessor 123 or 132 may take into account one or more patient and environmental factors (e.g. intermittent measurement schedule, health of the patient, transmission schedule, etc.) when dynamically deciding the priority to assign the intermittent measurement and the transmission.

Figure 8:
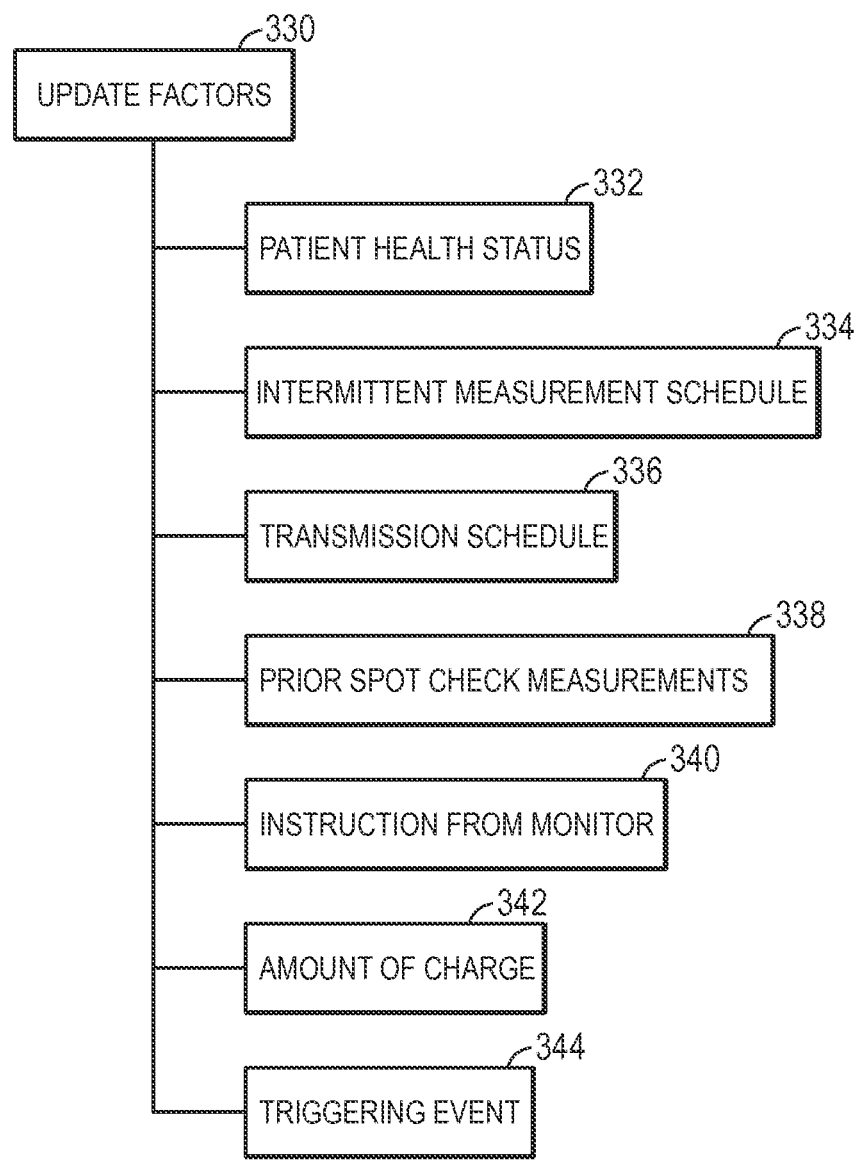
FIG. 8 is a schematic diagram of various factors that may be utilized with the method of FIG. 7, in accordance with an embodiment.

Indeed, FIG. 8 is a schematic diagram of various factors that may be utilized with the method 308 of FIG. 7, in accordance with an embodiment. It should be noted that none of the factors may be dispositive and the microprocessor 123 or 132 may take into account one or more of the factors when determining the priority of performing an intermittent measurement or data transmission.

A first factor 332 of the priority factors 330 may be the health status of the patient. The patient's health status may be determined by the microprocessor 123 or 132 by analyzing previously stored measurements in the non-volatile memory 127 or by performing a measurement and analyzing the results. If, for example, the patient's pulse rate is abnormally high, this factor 332 may weigh in favor of transmitting data to the monitor 102 in order for the monitor 102 to warn the clinician that the patient may be in danger. Likewise, if the patient's pulse rate is abnormally high, this factor may weigh against performing an intermittent measurement. This may be because the sensor 114 may only have enough energy to perform a measurement or transmit data and it may be more important to transmit the pulse rate data to the monitor 102 in order to warn the clinician. Thus, this factor 332 may increase the transmission's priority and decrease the intermittent measurements's priority. On the other hand, if the patient's measurements are within acceptable ranges, this factor 332 may weigh in favor of performing an intermittent measurement and weigh against transmitting data because there may not be as big of a need to alert the clinician that the patient 117 is doing well.

A second factor 334 of the priority factors 330 may be an intermittent measurement schedule. For example, if the microprocessor 123 or 132 determines that the next scheduled intermittent measurement is very near in time, this factor 334 may weigh in favor of transmitting previous measurements that may have been stored in the non-volatile memory 127. Thus, the transmission's priority may be increased. However, if the next scheduled intermittent measurement is not for a long time, this may weigh in favor of performing an intermittent measurement and the intermittent measurement's priority may be increased. This is especially important when a patient is on the cusp of being in danger (e.g., increasing pulse rate) and readings closer in time are important to safely monitor the patient's well being.

A third factor 336 of the priority factors 330 may be a transmission schedule. Like the intermittent measurement schedule, the transmission schedule may provide important information for the microprocessor 123 or 132 when determining the priority of the intermittent measurement and the transmission. For example, if the last transmission occurred a long time ago, it may be important to transmit the measurements that have since taken place. Thus, this factor 336 may weigh in favor of increasing the transmission's priority. However, if the last transmission occurred recently, this factor may weigh against transmitting data and in favor of performing an intermittent measurement. Thus, this factor 336 may increase an intermittent measurement's priority accordingly.

A fourth factor 338 of the priority factors 330 may be prior measurements. For example, if prior measurements indicate that the blood oxygen saturation and/or pulse rate are abnormal, it may be more important to transmit that information to the monitor 102 in order to alert a clinician.

Thus, the transmission's priority may be increased. However, if the prior measurements are within acceptable ranges, this factor 338 may weigh in favor of performing an intermittent measurement and against transmitting data because there is not a need to alert the clinician. Further, there may only be enough energy stored in the power source 160 to either perform an intermittent measurement or transmit data. In such a case, it may be more beneficial to perform another intermittent measurement to determine whether the measurements remain acceptable.

A fifth factor 340 of the priority factors 330 may be instructions from the monitor 102. For example, if a clinician presses a button on the monitor 102 to update the measurements, the monitor 102 may send a request to the sensor 114. This request may either notify the sensor 114 to send the most recent measurements or it may request that the sensor 114 perform an intermittent measurement and transmit the data as soon as possible. Thus, depending on the instructions from the monitor 102, the data transmission or intermittent measurement's priority may be increased or decreased accordingly.

A sixth factor 342 of the priority factors 330 may be an amount of charge stored in the power source 160. Transmitting data may require more energy than performing an intermittent measurement, or vice versa. Thus, if the amount of charge in the power source 160 is low, this factor 342 may weigh in favor of performing an intermittent measurement because it may not even be possible to transmit data. On the other hand, if the amount of charge stored in the power source 160 is sufficient to transmit data, this factor 342 may weigh in favor of transmitting data and against performing an intermittent measurement. Thus, the data transmission's priority may be increased.

As mentioned, this factor 342, along with the other factors, may be considered in conjunction with any of the previously mentioned factors. To illustrate, this factor 342 may weigh against performing data transmission because there is insufficient energy to transmit. However, factor 336 may weigh in favor of transmission because the last transmission occurred a long time ago. Thus, the microprocessor 123 or 132 may determine that even though this factor 342 weighs in favor of performing an intermittent measurement and against transmission, the other factor 336 that weighs in favor of transmission carries more weight in this scenario. Therefore, the microprocessor 123 or 132 may determine that it is more important to continue harvesting energy until a sufficient amount is stored to transmit data. Further, postponing performing an intermittent measurement to obtain enough energy to transmit data may become more important when the patient's health status (factor 332) is poor and transmitting that information to the monitor 102 is crucial to alert the clinician.

A seventh factor 344 of the priority factors 330 may be a triggering event. In certain embodiments, there are various triggering events that may increase the priority of the intermittent measurement or data transmission. For example, an intermittent measurement may be triggered when a patient is undergoing a cardiac stress test and is wearing a pulse oximeter sensor 114 that is measuring the patient's blood oxygen saturation and pulse rate. Thus, the intermittent measurement's priority may be increased in order to continuously monitor the patient's physiological parameters during the stress test. A triggering event that may increase the transmission's priority may be when an intermittent measurement is performed and abnormal results are obtained by the sensor 114. It should be noted that the same event that triggers an intermittent measurement may also generate the energy required to perform the measurement. Take, for example, the cardiac stress test scenario mentioned. An ambulatory sensor 114 designed to record data during the cardiac stress testing may collect charge and switch on by harvesting the kinetic energy of the patient 117 undergoing the test.

Returning to FIG. 7, specifically step 316, after the microprocessor 123 or 132 has determined the priority of performing the intermittent measurement and data transmission, it may determine which has a higher priority. As may be seen, if the transmission of data has a higher priority, the method moves to step 318 where the charging control circuit 162 determines the power source 160 energy level (e.g. amount of harvested energy) and the microprocessor 123 or 132 determines whether there is enough energy to transmit data. If there is not enough energy to transmit, the method 308 returns to step 309 to harvest energy. If there is enough energy to transmit, the transceiver 125 may transmit the measurement data and/or other data in step 320.

However, if the microprocessor 123 or 132 determines that the transmission does not have a higher priority than performing an intermittent measurement, the charging control circuit 162 determines the power source 160 energy level (e.g. amount of harvested energy) and the microprocessor 123 or 132 determines whether there is enough charged energy to perform an intermittent measurement (step 322). If there is not enough energy to perform an intermittent measurement, the method 308 returns to step 309 to harvest energy. If there is enough energy to perform an intermittent measurement, the microprocessor 123 or 132 may send a signal to the light drive circuitry 128 (via transceivers 112 and 125) to operate the emitter 116 and perform a measurement, as shown in step 324. In step 326, after the intermittent measurement is performed, the measurement data may be stored in the non-volatile memory 127.

Once either data is transmitted according to step 320 or data is stored according to step 326, the method 308 may return to step 314 to determine the priority of performing an intermittent measurement or transmitting data. As may be appreciated, the priority factors may have changed since the determination was made last time. In particular, the patient's health status may be updated if a measurement was performed, the intermittent measurement schedule may be updated, the transmission schedule may be updated, and so forth. As may be seen, the method 308 may continue to cycle through appropriate steps until there is insufficient energy to perform an intermittent measurement and/or transmit data. At such time, the method 308 returns to step 309 to harvest more energy.

Figure 9:
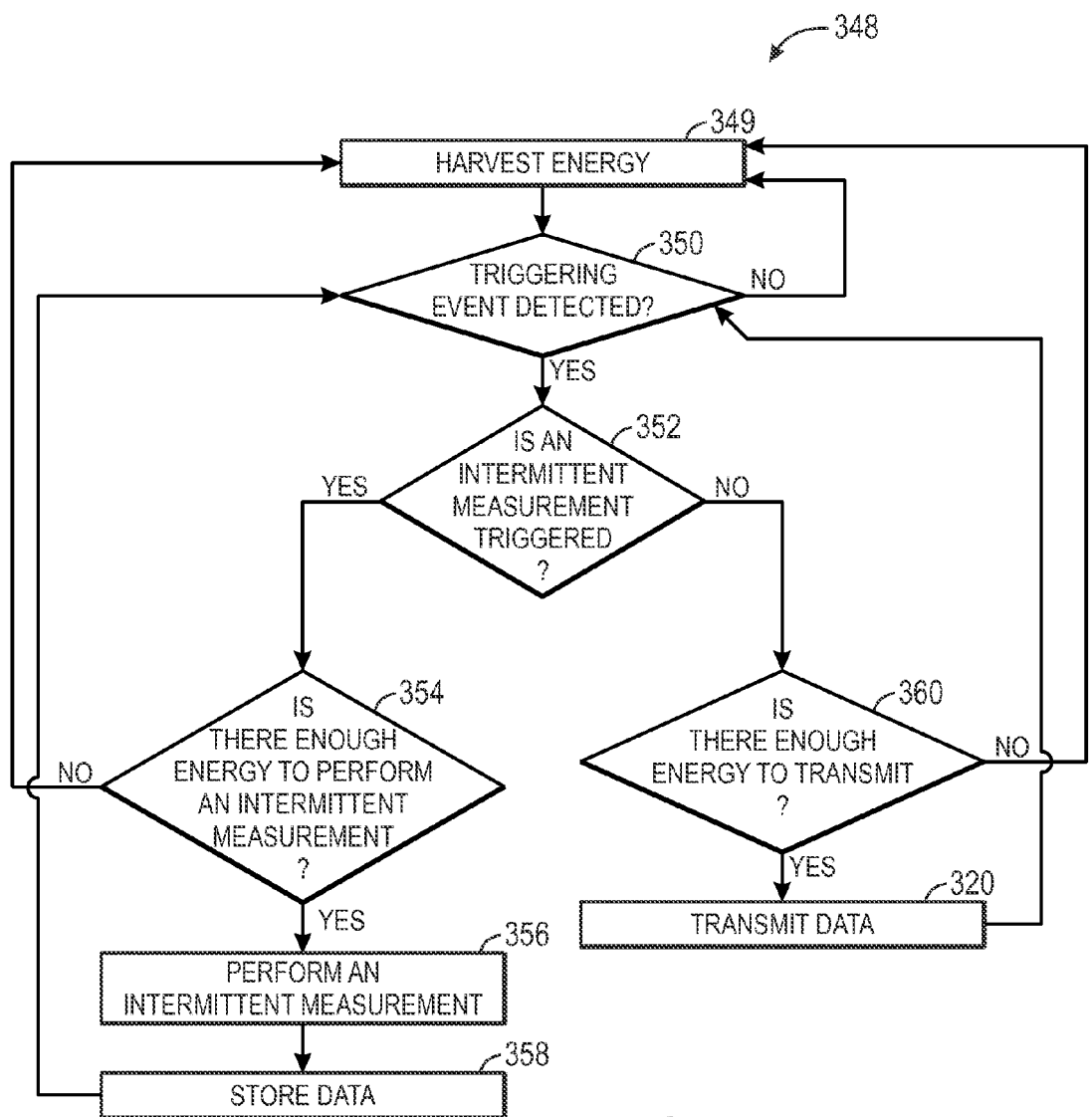
FIG. 9 is a flowchart describing an embodiment of a method for utilizing energy harvesting to perform intermittent operations based upon triggering events.

Turning to FIG. 9, which is a flowchart describing yet another embodiment of a method 348 for utilizing energy harvesting to perform intermittent measurements and transmit data. The method 348 begins at step 349 by harvesting energy to store in the power source 160. In step 350, the microprocessor 123 or 132 determines whether a triggering event is detected. As previously discussed, triggering events may vary for performing intermittent measurements and transmitting data. For example, a cardiac stress test may trigger an intermittent measurement and an abnormal measurement may trigger a transmission. If a triggering event is not detected, the method 348 returns to step 349 to continue harvesting energy. However, if a triggering event is detected, the microprocessor 123 or 132 may determine whether the event triggers an intermittent measurement in step 352. If an intermittent measurement is triggered, a determination may be made by the charging control circuit 162 of the amount of energy harvested (e.g. power source 160 energy level) and by the microprocessor 123 or 132 of whether there is sufficient energy stored in the power source 160 to perform the intermittent measurement (step 354). If there is insufficient energy stored, the method 348 returns to step 349 to harvest energy. However, if there is sufficient energy stored, the method proceeds to step 356 to perform the intermittent measurement and to step 358 to store the data in the non-volatile memory 127. After the data is stored, the method may return to monitoring whether a triggering event is detected.

If an intermittent measurement is not triggered at step 352, the method 348 may proceed to step 360 to determine whether there is enough energy stored in the power source 160 to transmit the measurement data and other data. If there is insufficient energy stored, the method 348 may return to step 349 to harvest energy. However, if there is sufficient energy stored, the microprocessor 123 may signal the transceiver 125 to transmit the measurement data and other data to the monitor 102.

Figure 10:
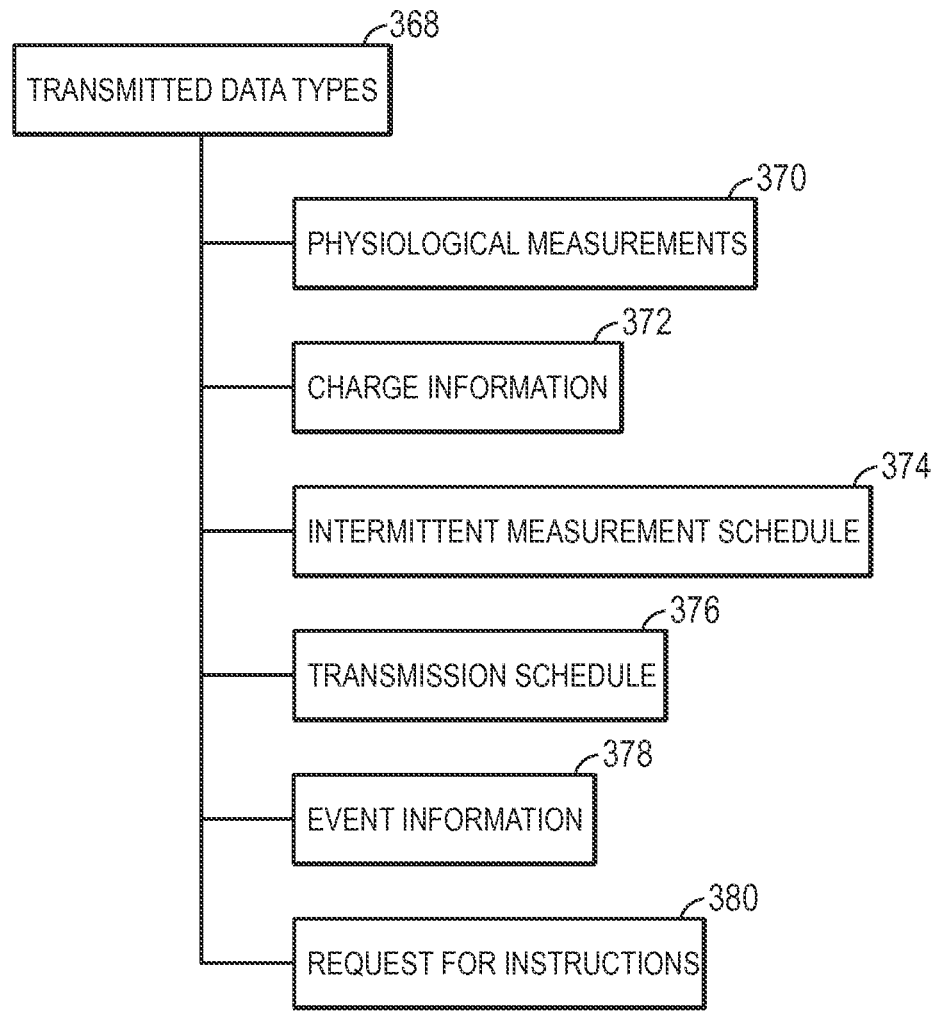
FIG. 10 is a schematic diagram of various data that may be utilized with the methods of FIGS. 5, 7, and 9, in accordance with an embodiment.

Example embodiments of data types that may be transmitted with the methods of FIGS. 5, 7, and 9 are depicted in the schematic diagram in FIG. 10. A first type of data 370 of the transmitted data types 368 may be physiological measurements. As previously discussed, these measurements may include pulse rate, respiration rate, blood oxygen saturation, patient temperature, among others. A second type of data 372 of the transmitted data types 368 may be charge information. For example, the sensor 114 may communicate wirelessly with the monitor 102 the degree to which the sensor 114 is charged, type of battery-less power source 160, type of energy harvesting technique utilized, and so forth. This may be useful for the monitor 102 in determining what instructions to provide to the sensor 114. For example, if the sensor 114 is very low on charge, the monitor 102 may not issue an instruction to transmit data because transmission may require more energy available in the sensor 114.

A third type of data 374 of the transmitted data types 368 may be an intermittent measurement schedule 374. The intermittent measurement schedule may include information such as the next scheduled intermittent measurement, the last measurement time, the rate at which intermittent measurements are being performed, and so forth. The intermittent measurement schedule may be useful to the monitor 102 in determining whether to send out a request for measurements if the next scheduled intermittent measurement is not due for a while or to wait until the next scheduled intermittent measurement. Further, a fourth type of data 376 of the transmitted data types 368 may be a transmission schedule 376. Like the intermittent measurement schedule, the transmission schedule 376 may be beneficial to the monitor 102 when it is determining when to send a request to the sensor 114 to transmit data. For example, if the next scheduled transmission is not to occur for a while, the monitor 102 may request the sensor 114 to transmit data before the scheduled time.

A fifth type of data 378 of the transmitted data types 368 may be event information. As previously discussed there may be various events that trigger an intermittent measurement or data transmission. The information associated with the triggering events may be useful for the monitor 102 when it is analyzing the measurements. For example, a cardiac stress test may trigger an intermittent measurement, which may record an elevated pulse rate. Instead of determining that the patient is in danger due to the elevated pulse rate, the monitor 102 may determine that the elevated pulse rate is normal in light of the cardiac stress test and that the patient is fine. A sixth type of data 380 of the transmitted data types 368 may be a request for instructions from the monitor 102. In some embodiments, a sensor 114 may request the monitor 102 to provide it with an intermittent measurement schedule and/or transmission schedule, among other things.

It should be noted that the above mentioned types of data that may be transmitted 368 by the sensor 114 are exemplary only and not exclusive. Each type of data may be transmitted individually or in any combination with the other types discussed.

Additionally, it should be appreciated that the methods 250, 308, and 348 discussed above may be combined in further embodiments. For example, a method may include a charging device 115 encapsulated in a sensor 114 harvesting energy and the sensor 114 performing an intermittent measurement based upon one or more of a power source 160 charge level, a determined intermittent measurement rate, a determined intermittent measurement priority, or an intermittent measurement triggering event. Likewise, the embodiment may involve the transceiver 125 transmitting data to the monitor 102 based upon one more of a power source 160 charge level, a determined transmission rate, a determined transmission priority, or a transmission triggering event.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A medical sensor, comprising:
a battery-less power source configured to store energy;
a charging device configured to harvest energy from body heat, body movement, or ambient light and to charge the power source;
a charging control circuit configured to determine a power source energy level of the power source;
a sensing component configured to perform an intermittent measurement to obtain data related to one or more physiological parameters from a patient;
wireless communication circuitry configured to wirelessly transmit at least the data related to the one or more physiological parameters; and
a processing device configured to determine if the power source energy level is sufficient to perform the intermittent measurement or to wirelessly transmit at least the data related to the one or more physiological parameters and to determine whether to perform the intermittent measurement or to wirelessly transmit at least the data related to the one or more physiological parameters based upon the power source energy level and a prioritization of the intermittent measurement relative to wireless transmission of at least the data related to the one or more physiological parameters.

2. The medical sensor of claim 1, wherein the medical sensor is configured to asynchronously perform the intermittent measurement and to wirelessly transmit at least the data related to the one or more physiological parameters.

3. The medical sensor of claim 1, wherein the processing device is configured to prioritize between performing the intermittent measurement and wirelessly transmitting at least the data related to the one or more physiological parameters based on one or more of a health status of the patient and values of physiological parameters obtained from one or more previous intermittent measurements.

4. The medical sensor of claim 1, wherein the processing device is configured to prioritize between performing the intermittent measurement and wirelessly transmitting at least the data related to the one or more physiological parameters based on one or more of when the intermittent measurement is next scheduled and when a last transmission of at least the data related to the one or more physiological parameters occurred.

5. The medical sensor of claim 1, comprising a memory, and the processing device is configured to store at least the data related to the one or more physiological parameters on the memory if the power source energy level is not sufficient to wirelessly transmit at least the data related to the one or more physiological parameters.

6. The medical sensor of claim 5, wherein the processing device is configured to cause wireless transmission of at least the data related to the one or more physiological parameters upon the power source energy level being sufficient for transmission.

7. The medical sensor of claim 1, wherein the battery-less power source comprises a capacitor or an inductor.

8. The medical sensor of claim 1, comprising an indicator configured to provide a visual indication, audio indication, or any combination thereof, that the power source has stored a certain amount of charge.

9. The medical sensor of claim 1, wherein the processing device is configured to:
  determine a respective priority of the intermittent measurement and a respective priority of the of the wireless transmission of at least the data related to the one or more physiological parameters based on one or more factors;
  compare the respective priority of the intermittent measurement to the respective priority of the wireless transmission of at least the data related to the one or more physiological parameters to determine the prioritization;
  perform the intermittent measurement in response to determining that the power source energy level is sufficient for the intermittent measurement and that the respective priority of the intermittent measurement exceeds the respective priority of the wireless transmission of at least the data related to the one or more physiological parameters; and
  wirelessly transmit at least the data related to the one or more physiological parameters in response to determining that the power source energy level is sufficient for the wireless transmission and that the respective priority of the wireless transmission of at least the data related to the one or more physiological parameters exceeds the respective priority of the intermittent measurement.

10. A monitoring system, comprising:
  a battery-less wireless medical sensor; and
  a monitor, comprising:
    wireless communication circuitry configured to wirelessly transmit at least a request for an intermittent measurement to collect data related to one or more physiological parameters to the battery-less wireless medical sensor and a request for a wireless transmission of the data related to the one or more physiological parameters to the battery-less wireless medical sensor, and to receive at least information relating to a power source of the battery-less wireless medical sensor from the battery-less wireless medical sensor and the data related to the one or more physiological parameters from the battery-less wireless medical sensor;
    a detector/decoder configured to decode the information received from the battery-less wireless medical sensor and relay it to a processing device; and
    a memory configured to store operational algorithms;
    wherein the processing device is configured to use the operational algorithms to make the requests to the battery-less wireless sensor for intermittent measurements and wireless transmissions of data related to the one or more physiological parameters from the battery-less wireless medical sensor based upon the information relating to the power source of the battery-less wireless medical sensor.

11. The monitoring system of claim 10, wherein the battery-less wireless medical sensor is configured to wirelessly transmit the information relating to the power source to the monitor in response to wireless communication with the monitor being established.

12. The monitoring system of claim 10, wherein the information relating to the power source of the battery-less wireless medical sensor comprises at least one of an amount of charge available in the power source of the battery-less wireless medical sensor, an amount of energy used to perform the intermittent measurement and the wireless transmission of at least the data related to the one or more physiological parameters, a proper charging technique for the power source, a type of the power source, a length of time that fully charges the power source, and whether the power source is charging.

13. The monitoring system of claim 10, wherein the processing device is configured to prioritize between performing the intermittent measurement and wirelessly transmitting at least the data related to the one or more physiological parameters based on one or more factors.

14. The monitoring system of claim 13, wherein the one or more factors comprise a health status of the patient, when the intermittent measurement is next scheduled, when a last transmission of at least the data related to the one or more physiological parameters occurred, and values of physiological parameters obtained from one or more previous intermittent measurements.

15. The monitoring system of claim 10, wherein the processing device is configured to download software updates based upon the information relating to the power source of the battery-less wireless medical sensor to download and store the operational algorithms to the memory.

16. A method for a monitoring system, comprising:
  charging, using a charging device, a power source for a battery-less wireless medical sensor by harvesting energy from body heat, body movement, or ambient light;
  determining, using a charging control circuit, a power source energy level of the power source; and
  determining, using a processing device of the battery-less wireless medical sensor, whether to perform, using a sensing component of the battery-less wireless medical sensor, an intermittent measurement to obtain data related to one or more physiological parameters from a patient, to wirelessly transmit to a monitor, using wireless communication circuitry of the battery-less wireless medical sensor and the monitor, at least the data related to the one or more physiological parameters, or both, based upon the power source energy level, and a prioritization of the intermittent measurement relative to wireless transmission of at least the data related to the one or more physiological parameters.

17. The method of claim 16, comprising wirelessly transmitting at least the data related to the one or more physiological parameters from the battery-less wireless medical sensor to the monitor in response to identifying a sufficient power source energy level and determining that a respective priority of the wireless transmission of at least the data related to the one or more physiological parameter exceeds a respective priority of the intermittent measurement.

18. The method of claim 16, comprising determining, using the processing device, the prioritization of the intermittent measurement relative to wireless transmission of at least the data related to the one or more physiological parameters to the monitor based on one or more factors comprising a health status of the patient, when the intermittent measurement is next scheduled, when a last transmission of at least the data related to the one or more physiological parameters occurred, and values of physiological parameters obtained from one or more previous intermittent measurements.

19. The method of claim 18, comprising storing at least the data related to one or more physiological parameters on a memory of the battery-less wireless medical sensor for later transmission to the monitor in response to the power source energy level not being sufficient to wirelessly transmit at least the data related to the one or more physiological parameters to the monitor.

20. The method of claim 16, wherein determining whether to perform the intermittent measurement, to wirelessly transmit at least the data related to the one or more physiological parameters, or both, is based upon one or more of an intermittent measurement rate, a transmission rate, or a triggering event.

* * * * *